United States Patent [19]
Ara et al.

[11] Patent Number: 5,635,468
[45] Date of Patent: Jun. 3, 1997

[54] LIQUEFYING ALKALINE α-AMYLASE, PROCESS FOR PRODUCING THE SAME, AND DETERGENT COMPOSITION CONTAINING THE SAME

[75] Inventors: Katsutoshi Ara, Oyama; Katsuhisa Saeki, Kawachi-machi; Kazuaki Igarashi, Kaminokawa-machi; Mikio Takaiwa, Tochigi; Takaaki Uemura, Hazaki-machi; Shuji Kawai, Kawachi-machi; Susumu Ito, Utsunomiya; Hiroshi Hagihara, Ichikai-machi; Tohru Kobayashi, Utsunomiya; Atsushi Tanaka; Eiichi Hoshino, both of Wakayama, all of Japan

[73] Assignee: Kao Corporation, Tokyo, Japan

[21] Appl. No.: 362,493

[22] PCT Filed: May 19, 1994

[86] PCT No.: PCT/JP94/00805

§ 371 Date: Jan. 11, 1995

§ 102(e) Date: Jan. 11, 1995

[87] PCT Pub. No.: WO94/26881

PCT Pub. Date: Nov. 24, 1994

[30] Foreign Application Priority Data

May 19, 1993 [JP] Japan ................................. 5-117392

[51] Int. Cl.$^6$ .................................................. C11D 3/386
[52] U.S. Cl. ........................... 510/392; 510/531; 435/201; 435/202; 435/203; 435/204
[58] Field of Search ................. 252/174.12, DIG. 12; 435/201, 202, 203, 204; 510/392, 530

[56] References Cited

U.S. PATENT DOCUMENTS

| | | | |
|---|---|---|---|
| 4,284,722 | 8/1981 | Tamuri et al. | 435/94 |
| 4,469,791 | 9/1984 | Colson et al. | 435/253 |
| 4,642,288 | 2/1987 | El. DeMiguel et al. | 435/99 |
| 4,724,208 | 2/1988 | Brewer et al. | 252/188 |
| 5,030,377 | 7/1991 | Sone et al. | 252/174.12 |
| 5,173,207 | 12/1992 | Drapier et al. | |
| 5,188,956 | 2/1993 | Nanmori et al. | 435/200 |
| 5,316,691 | 5/1994 | Sone et al. | 252/174.12 |
| 5,364,782 | 11/1994 | Quax et al. | |
| 5,429,766 | 7/1995 | Son et al. | 252/174.12 |

FOREIGN PATENT DOCUMENTS

| | | |
|---|---|---|
| 410498 | 1/1991 | European Pat. Off. |
| 516553 | 12/1992 | European Pat. Off. |
| WO8905863 | 6/1989 | WIPO |
| WO9100353 | 1/1991 | WIPO |
| WO9402597 | 2/1994 | WIPO |
| WO95/26397 | 10/1995 | WIPO |

*Primary Examiner*—Paul Lieberman
*Assistant Examiner*—Kery A. Fries
*Attorney, Agent, or Firm*—Oblon, Spivak, McClelland, Maier & Neustadt, P.C.

[57] ABSTRACT

The present invention relates to a liquefying alkaline α-amylase having the enzymatic properties described below, a production process thereof and a detergent composition containing the same.

1) Action:

It hydrolyzes α-1,4-glucosidic linkages in starches, amylose, amylopectin and partial degradation products thereof and from amylose, forms glucose (G1), maltose (G2), maltotriose (G3), maltotetraose (G4), maltopentaose (G5) and maltohexaose (G6). It however does not act on pullulan.

2) Isoelectric point:

It has an isoelectric point higher than 8.5 when measured by an isoelectric focusing electrophoresis.

The amylase according to the present invention has a liquefying activity capable of permitting degrading starches and starchy polysaccharides at high random, and has an optimum pH on the alkaline side. Owing to the high isoelectric point, it can be purified readily. Detergents with the amylase incorporated therein have excellent detergency especially against the soil of smeared food.

23 Claims, 5 Drawing Sheets

LIQUEFYING ALKALINE α-AMYLASE, PROCESS FOR PRODUCING THE SAME, AND DETERGENT COMPOSITION CONTAINING THE SAME

TECHNICAL FIELD

This invention relates to liquefying alkaline α-amylases useful as components for detergents, a preparation process thereof and detergent compositions containing the same.

BACKGROUND ART

α-Amylases are enzymes which hydrolyze only α-1,4-glucosidic linkages in molecules of starchy polysaccharides such as starches, amylose and amylopectin. Since the discovery of an α-amylase from a malt extract by Payen and Persoz in 1833, they have been obtained as crystalline samples or electrophoretically uniform samples from various living organisms, for example, bacteria belonging mainly to the genus Bacillus, such as *Bacillus subtilis Marburg*, *Bacillus subtilis natto*, *Bacillus amyloliquefaciens*, *Bacillus licheniformis*, *Bacillus cereus*, *Bacillus circulans*, *Bacillus macerans*, *Pseudomonas stutzeri* and *Klebsiella aerogenes;* Actinomycetes such as *Streptomyces griseus;* molds belonging mainly to the genus Aspergillus such as *Aspergillus oryzae* and *Aspergillus niger;* seeds of gramineous and leguminous plants; and digestive glands of animals such as human and swine.

α-Amylases have been used widely for many years, for example, for the saccharification of grains and potatoes in the brewing industry, as a desizing agent in the fiber industry, as a high-efficacy digestive in the pharmaceutical industry and for the production of thick malt syrup in the food industry.

The present inventors previously found that the incorporation of such an α-amylase in a dish washing detergent or in a laundry detergent together with a debranching enzyme makes it possible to prepare a detergent having significantly improved detergency against starch stains and already filed a patent application thereon (Japanese Patent Laid-Open No. 132192/1990).

Most of α-amylases which have heretofore been found in the natural world exhibit maximum and stable enzymatic activity in a neutral to acidic range, in other words, are classified as neutral to acidic α-amylases, leading to the drawback that their activity is deteriorated in a surfactant-containing solution whose pH is on the alkaline side. On the other hand, α-amylases exhibiting maximum activity in the alkaline range or having alkali resistance, in other words, alkaline α-amylases and alkali-resistant α-amylases are free of the above drawback and are useful as components for detergents. Known examples of such alkaline amylases and alkali-resistant α-amylases are limited only to the enzyme produced by the strain *Bacillus sp.* A-40-2 [Agric. Biol. Chem., 35, 1783 (1971)], the enzyme produced by the strain *Bacillus sp.* NRRL B-3881 [J. Bacteriol., 110, 992 (1972)], the enzyme produced by *Streptomyces sp.* KSM-9 (Japanese Patent Laid-Open No. 209588/1986, the enzyme produced by the strain *Bacillus sp.* H-167 (Japanese Patent Laid-Open No. 208278/1987), the enzyme produced by the strain *Bacillus alcalothermophilus* A3-8 (Japanese Patent Laid-Open No. 49584/1990) and the enzyme produced by the strain *Natrococcus sp.* Ah-36 (Japanese Patent Laid-Open No. 211369/1992). Incidentally, the term "alkaline α-amylase" as used herein means an α-amylase whose optimum pH is in an alkaline range, while the term "alkali-resistant α-amylase" means an α-amylase which has an optimum pH in a neutral to acidic range, but even in an alkaline range, can still exhibit activity comparable with that at an optimum pH and retains stability. The term "neutral" as used herein means a pH range of from 6 to 8 and "alkaline" means a pH range higher than the above range.

To the best of the present inventors's knowledge, these alkaline and alkali-resistant enzymes belong to so-called saccharifying α-amylases which degrade starches or starchy polysaccharides to glucose, maltose or maltotrise. They are hence suited as enzymes for the production of sugar but not as enzymes for detergents. Paying attention to so-called liquefying α-amylases which are resistant to surfactants and in addition, degrade starches or starchy polysaccharides at high random, the present inventors have proceeded with an investigation. As a result, it has been found that conventionally known alkaline α-amylases are only those showing the characteristics of the saccharifying type and there is absolutely no report on liquefying alkaline α-amylases.

Furthermore, to obtain the conventional alkaline α-amylases, purification of several steps is required. This purification is not satisfactory as a purification method for enzymes on an industrial scale. With a view toward obtaining a purified enzyme easily by using the characteristics of enzymes, the present inventors paid attention to an enzymatic protein having a high surface charge. As a result, it was found that all the alkaline α-amylases known to date have an isoelectric point of about 3.0–8.0 and there is utterly no report on alkaline α-amylases having an isoelectric point exceeding 8.5 as in the present invention, An object of the present invention is therefore to provide an α-amylase which has resistance to surfactants, has an optimum pH in an alkaline range, is of a liquefying type, that is, degrades starches or starchy polysaccharides at high random and has a high isoelectric point; and also a detergent composition containing the α-amylase.

DISCLOSURE OF THE INVENTION

Under the aforementioned circumstances, the present inventors have proceeded with an extensive search with a view toward finding out from the natural world a microorganism which produces a liquefying alkaline α-amylase having the above-described properties. As a result, they have found a novel alkaline α-amylase having liquefying-type reaction characteristics in a culture of a microorganism belonging to the genus Bacillus, which was reported previously in Japanese Patent Laid-Open No. 108482/1991 as a microorganism which produces an enzyme having both an α-amylase activity and pullulanase activity and having a molecular weight of 200,000±5,000. They have also found that incorporation of the enzyme in a detergent can markedly improve detergency against combined stains of curry and ketchup spilt upon eating, leading to the completion of the invention.

The present invention therefore provides a liquefying alkaline α-amylase having the following enzymatic characteristics, a production process thereof and a detergent composition containing the same.

1) Action:

The liquefying alkaline α-amylase hydrolyzes α-1,4-glucosidic linkages in starches, amylose, amylopectin and partial degradation products thereof and from amylose, forms glucose (G1), maltose (G2), maltotriose (G3), maltotetraose (G4), maltopentaose (G5), and maltohexaose (G6). It however does not act on pullulan.

2) Isoelectric point:

It has an isoelectric point higher than 8.5 when measured by isoelectric focusing electrophoresis.

BEST MODES FOR CARRYING OUT THE INVENTION

Figure 1:
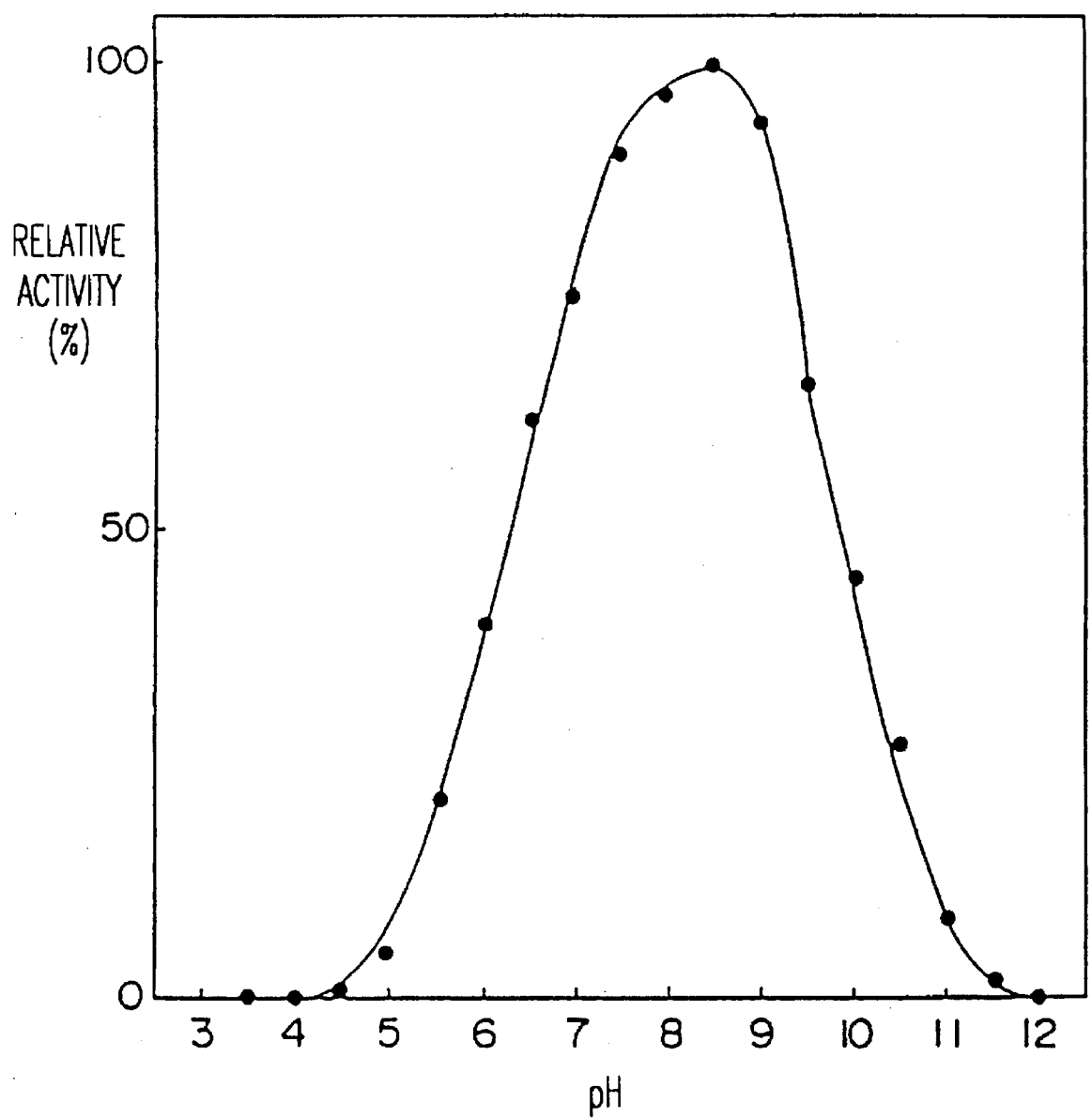
FIG. 1 diagrammatically illustrates the activity of the liquefying alkaline α-amylase according to the present invention as a function of pH.

It is preferred to control an optimum pH of the liquefying alkaline α-amylase of the present invention in a range of from 8.0 to 10.0 from the viewpoint that the α-amylase serves as a component for detergents.

No particular limitation is imposed on the microorganism which produces the liquefying alkaline α-amylase of the present invention, insofar as it has the capacity of producing the α-amylase having the property of degrading starches or starchy polysaccharides at high random, having an optimum pH in an alkaline range and having a high isoelectric point. Its examples include Bacillus sp. KSM-AP1378 (FERM BP-3048) belonging to the genus Bacillus and disclosed in Japanese Patent Laid-Open No. 108482/1991.

To obtain the liquefying alkaline α-amylase of the present invention by using the above strain, the strain may be inoculated on a medium and then cultured in a manner known per se in the art. It is preferred to incorporate proper amounts of some assimilable carbon and nitrogen sources in the medium. Although no particular limitation is imposed on the carbon and nitrogen sources, examples of the nitrogen sources include organic nitrogen sources such as corn gluten meal, soybean flour, corn steep liquor, casamino acid, yeast extract, pharmamedia, meat extract, trypton, soyton, hypro, ajipower, soybean meal, cotton seed oil cake, cultivator, ajipron and zest; and inorganic nitrogen sources such as ammonium sulfate, ammonium nitrate, ammonium phosphate, ammonium carbonate, sodium nitrate and ammonium acetate. Examples of the carbon sources include soluble starches, insoluble starches, amylopectin, glycogen, pullulan and oligosaccharides obtained by the partial degradation thereof, assimilable carbon sources such as glucose, maltose, arabinose, xylose, ribose, mannose, fructose, galactose, malt sugar, sucrose, lactose, trehalose, mannitol, sorbitol and glycerol and assimilable organic acids such as acetic acid. In addition, inorganic salts such as phosphates, magnesium salts, calcium salts, manganese salts, zinc salts, cobalt salts, sodium salts and potassium salts and, if necessary, inorganic and organic trace sources can be added as needed to the medium.

In accordance with general sampling and purifying means for enzymes, the liquefying alkaline α-amylase, that is, the target substance can be sampled from the cells so cultured and then purified. Namely, the microorganism bodies are removed from the culture medium by an ordinarily-employed solid-liquid separation means such as centrifugal separation or filtration, whereby the corresponding crude enzyme can be obtained in the form of a solution. The crude enzyme solution can be used neat. It can also be used as a purified enzyme after being separated by a separation means such as salting out, solvent precipitation, ultrafiltration or gel filtration as needed and then, making use of its high isoelectric point, subjecting the crude enzyme so separated to purification and crystallization by gel isoelectric focusing electrophoresis, density gradient isoelectric focusing electrophoresis, ion-exchange chromatography or the like.

The α-amylase of the present invention so obtained has an optimum pH in an alkaline range, has a high random degrading property—which means that it is of a liquefying type—and has a high isoelectric point. It has hence peculiar properties different from the conventional alkaline α-amylases. A description will next be made of various enzymatic properties of the liquefying alkaline α-amylase of the present invention obtained using strains of Bacillus sp. KSM-AP1378 (FERM BP-3048).

Incidentally, an enzyme activity was measured using the following buffers, each 40 mM, in accordance with the method described below.

pH 4–6 acetic acid buffer
pH 6–8 tris-hydrochloric acid buffer
pH 8–11 glycine-salt-sodium hydroxide buffer
pH 11–12 potassium chloride-sodium hydroxide buffer Measuring method of the enzyme activity (measurement of an amylase activity by DNS method):

To 0.9 ml of a buffer containing a soluble starch (product of Wako Pure Chemical Industries, Ltd., final concentration in the reaction system: 0.5%) dissolved therein, 0.1 ml of an enzyme solution was added, followed by the reaction at 40° C. for 30 min. After the reaction, reducing sugar was quantitatively analyzed by the 3,5-dinitrosalicylic acid (DNS) method. Described specifically, 1.0 ml of the DNS reagent was added to 1.0 ml of the reaction mixture, followed by color development under heating at 100° C. for 5 min. After being allowed to cool down, the reaction mixture was added with 4.0 ml of deionized water for dilution and was subjected to colorimetric determination at a wavelength of 535 nm. As the titer of the enzyme, the amount of the enzyme which formed reducing sugar equivalent to 1 μmol of glucose in one minute was defined as one unit (1 U).

(Various Enzymatic properties)
(1) Action

The liquefying alkaline α-amylase according to the present invention hydrolyzes α-1,4-glucosidic linkages in starches, amylose, amylopectin and partial degradation products thereof. It however does not act on pullulan.

Its actions on various substrates are shown in Table 1.

TABLE 1

| Substrate | Concentration (%) | Relative activity (%) |
| --- | --- | --- |
| Soluble starch (potato) | 0.25 | 100.0 |
| Amylose (corn) | 0.25 | 92.3 |
| Amylopectin (corn) | 0.25 | 86.6 |
| Amylopectin (potato) | 0.25 | 85.1 |
| Glycogen (oyster) | 0.25 | 73.2 |
| Dextrin | 0.25 | 0.0 |
| Dextran | 0.25 | 0.0 |
| Pullulan | 0.25 | 0.0 |

(2) Acting pH and optimum pH

It acts in a pH range of from about 5.0 to 11.0 and its optimum pH is 8.0–9.0 (FIG. 1).

(3) pH Stability

Figure 2:
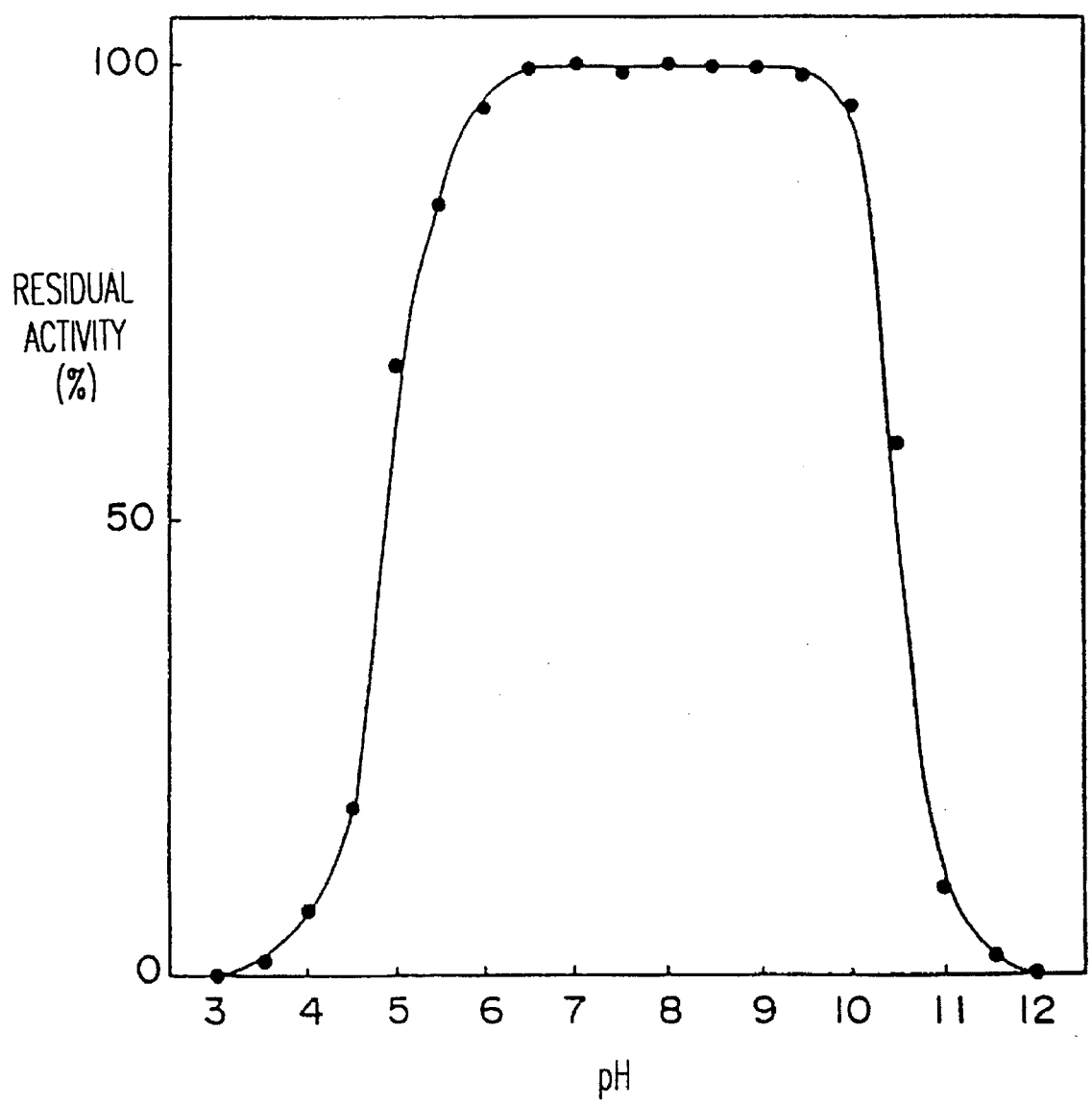
FIG. 2 diagrammatically illustrates the pH stability of the liquefying alkaline α-amylase according to the present invention.

It is extremely stable in a pH range of from 6.5 to 10. Even in a pH range of from 5 to 10.5, it retains at least about 50% of its activity (FIG. 2).

(4) Acting temperature range and optimum temperature

Figure 3:
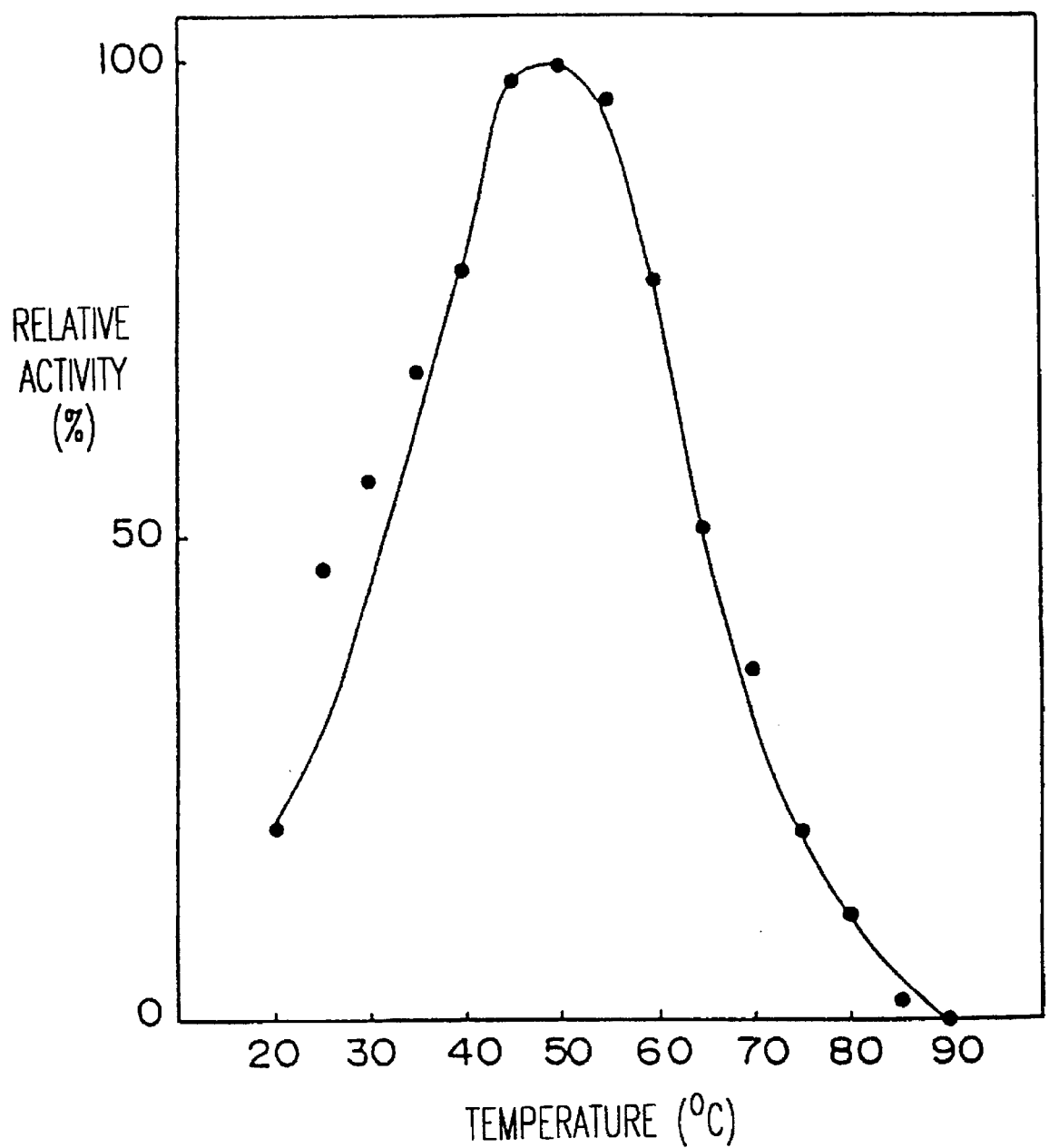
FIG. 3 diagrammatically depicts a temperature range in which the liquefying alkaline α-amylase according to the present invention can act.

It acts in a broad temperature range of from 20° to 80° C. and the optimum temperature is 45°–55° C. (FIG. 3).

(5) Thermal stability

Figure 4:
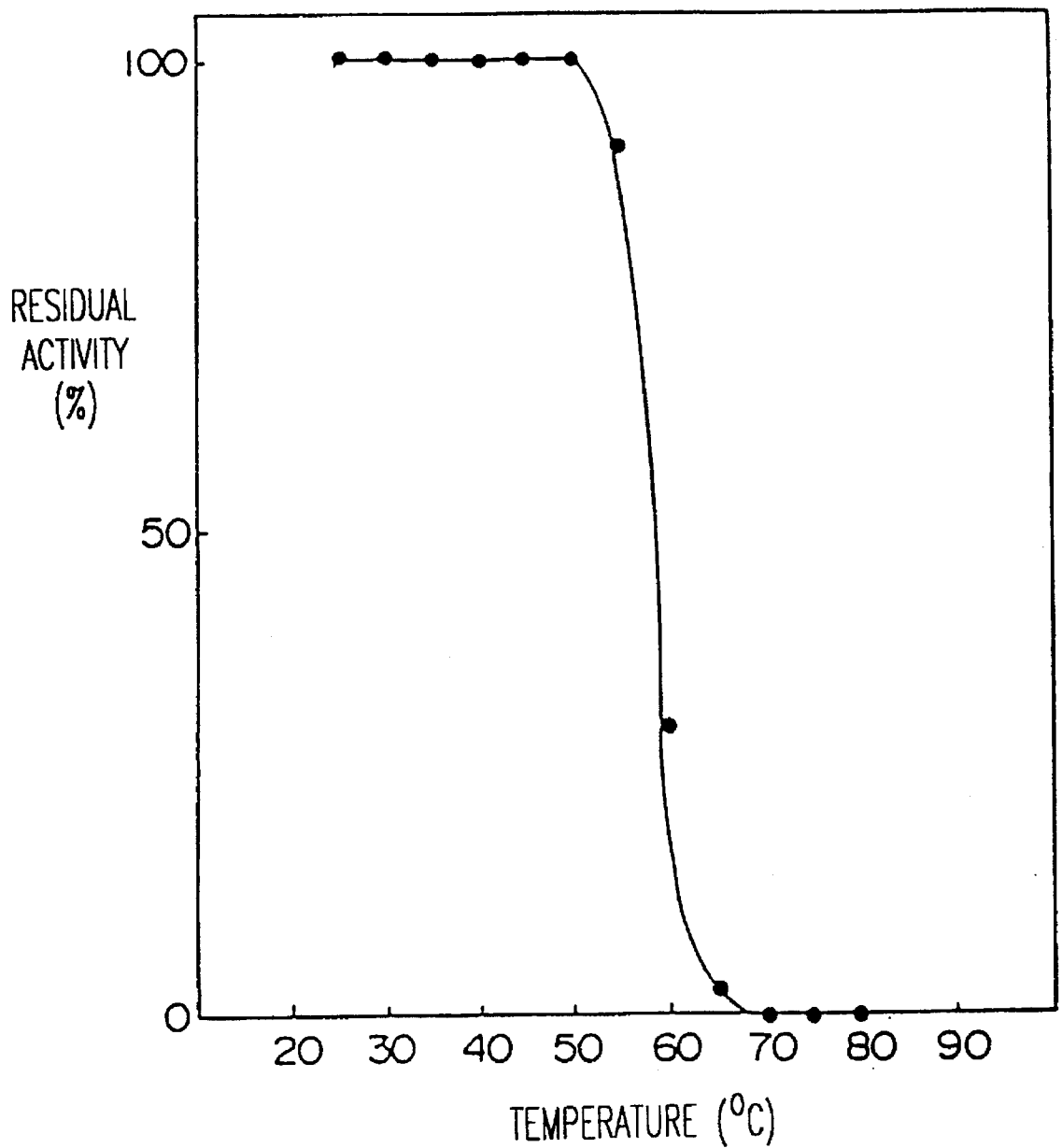
FIG. 4 diagrammatically depicts the thermal stability of the liquefying alkaline α-amylase according to the present invention.

Conditions for the inactivation of the present enzyme were studied by changing the temperature at pH 8.5 and treating it for 30 minutes at each temperature. As a result, it was found to be extremely stable up to 50° C. (FIG. 4).

(6) Molecular weight

Figure 5:
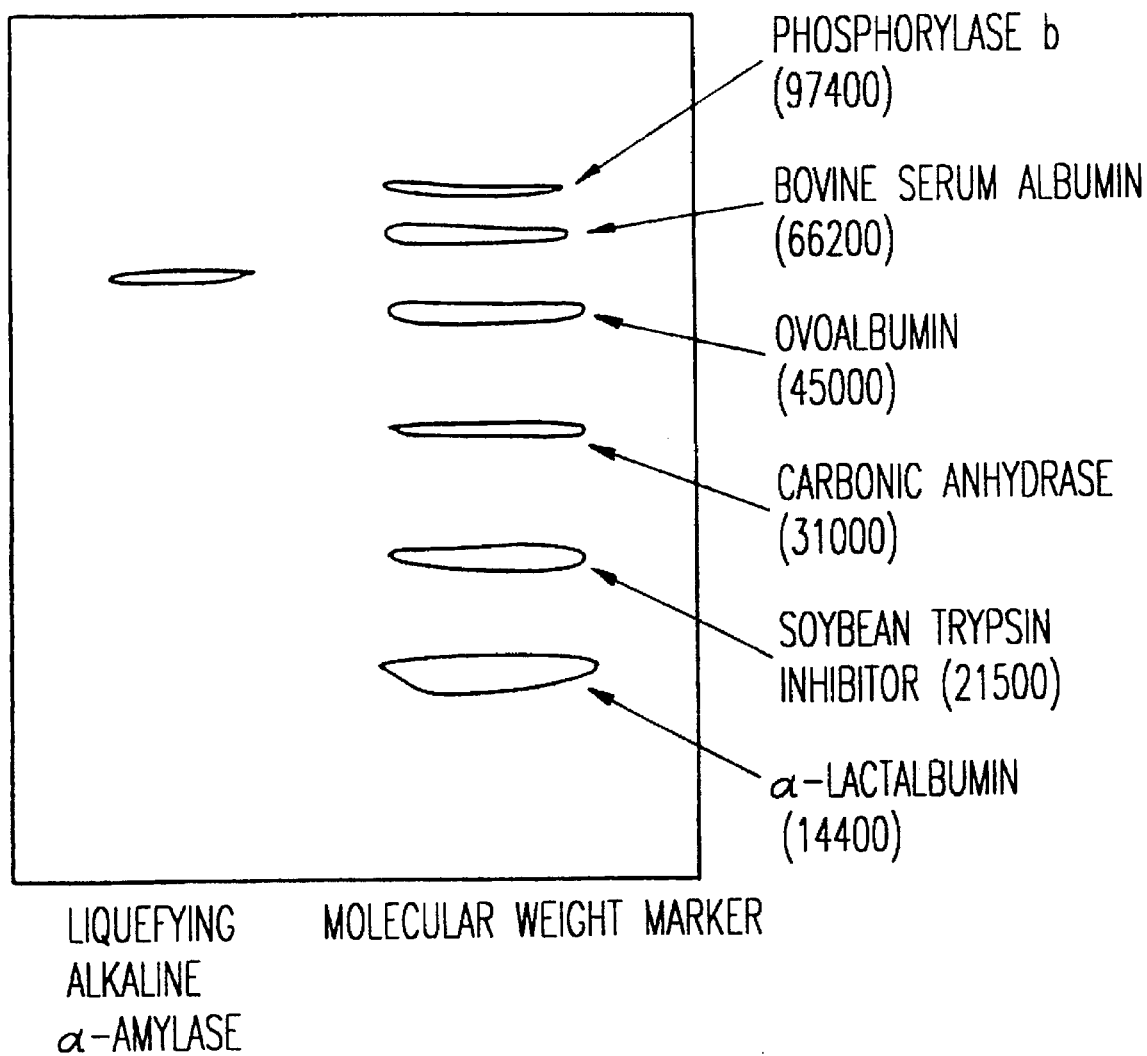
FIG. 5 diagrammatically shows the result of electrophoresis (12.5% polyacrylamide gel, treated at 95° C. for 4 min., quick CBB dyeing) of the liquefying alkaline α-amylase according to the present invention in a sodium dodecyl sulfate polyacrylamide gel.

Its molecular weight is 50,000±5,000 as measured by the sodium dodecyl sulfate polyacrylamide gel electophoresis (FIG. 5).

(7) Isoelectric point

Its isoelectric point is about 9.2 as measured by isoelectric focusing electrophoresis.

(8) Effects of metal salts

It was treated at 50° C. for 15 min. in each of reaction systems which contained the various metal salts shown in Table 2, respectively, whereby their effects were studied. As a result, the enzyme according to this invention was found to be extremely stable to metal ions commonly contained in tap water such as $K^+$, $Na^+$, $Ca^{2+}$, $Mg^{2+}$, $Mn^{2+}$, $Ba^{2+}$, $Fe^{2+}$, $Fe^{3+}$ and $Al^{3+}$.

TABLE 2

| Metal salt | Concentration (mM) | Residual activity (%) |
|---|---|---|
| KCl | 50 | 112.0 |
| NaCl | 50 | 109.1 |
| CaCl$_2$ | 1 | 96.8 |
| CuCl$_2$ | 1 | 102.9 |
| CoCl$_2$ | 1 | 62.5 |
| MnCl$_2$ | 1 | 116.9 |
| BaCl$_2$ | 1 | 108.7 |
| NiCl$_2$ | 1 | 27.2 |
| CdCl$_2$ | 1 | 19.5 |
| HgCl$_2$ | 1 | 0.0 |
| MgCl$_2$ | 1 | 106.7 |
| FeCl$_2$ | 1 | 114.4 |
| FeCl$_3$ | 1 | 93.2 |
| AlCl$_3$ | 1 | 101.5 |

(9) Actions of surfactant

Even when treated at 40° C. for 30 minutes with 0.05% solutions of various surfactants such as sodium linear alkylbenzenesulfonate (LAS), alkyl sulfate ester sodium salt (AS), polyoxyethylene alkylsulfate ester sodium salt (ES), sodium alkylsulfonate (SAS), soap and polyoxyethylene alkylether, it was almost free from activity inhibition.

(10) Hydrolysis rate of starch

The degradation rate of potato-derived starch is about 32%. In addition, it degrades amylose (polymerization degree: 117 glucose molecules) to glucose (G1), maltose (G2), malto triose (G3), malto tetraose (G4), malto pentaose (G5) and malto hexaose (G6).

(11) Analysis of N-terminal amino acid sequence

The N-terminal amino acid sequence of the present amylase was determined by Edman degradation [Edman, P., Acta Chem. Scand., 4, 283 (1948)] with a protein sequencer (model 477A manufactured by ABI Corp.). As a result, it was found to have, in the N-terminal region, a common sequence (Asn-Gly-Thr-Met-(Met)-Gln-Tyr-Phe-Glu-Trp) specific to the liquefying amylase. Incidentally, examples of literatures on the N-terminal region of the liquefying α-amylase include J. Biochem., 98, 1147–1156 (1985) and J. Biochem., 98, 95–103 (1985).

Each detergent composition according to the present invention may contain the above-described liquefying alkaline α-amylase in an amount of 1–10,000 U/g, more preferably 5–5,000 U/g, most preferably 10–1,000 U/g in terms of the activity for the degradation of potato-derived soluble starch.

Each detergent composition according to the present invention can further contain known detergent components, which will be exemplified below.

(1) Surfactants

Illustrative surfactants include anionic surfactants such as linear alkylbenzene sulfonates each of which contains at least one alkyl group having 10–16 carbon atoms on average, alkylethoxy sulfates each of which contains at least one linear or branched alkyl group having 10–20 carbon atoms on average and has 0.5–8 moles of ethylene oxide added per molecule, alkylsulfates each of which contains at least one alkyl group having 10–20 carbon atoms on average, olefinsufonates containing 10–20 carbon atoms on average per molecule, alkanesulfonates containing 10–20 carbon atoms on average per molecule, the methyl and ethyl esters of α-sulfo-fatty acids containing 10–20 carbon atoms on average per molecule, higher fatty acid salts having 8–20 carbon atoms on average and alkylether carboxylates each of which contains a linear or branched alkyl group having 10–20 carbon atoms on average and has 0.5–8 moles of ethylene oxide added per molecule; nonionic surfactants such as polyoxyethylene alkyl ethers each of which contains at least one alkyl group having 10–20 carbon atoms on average and has 1–20 moles of added ethylene oxide, higher fatty acid alkanol amides and alkylene-oxide adducts thereof, and ethylene-oxide adducts of propylene oxide-propylene glycol condensates which are known in the name of "Pullulonic"; betaine type amphoteric surfactants; sulfonic-acid-type amphoteric surfactants; phosphate ester type surfactants; amino acid type surfactants; and cationic surfactants.

These surfactants may be added in an amount of 0.5–60 wt. % (hereinafter referred to merely as "%") to the detergent composition. Described specifically, they can be added in an amount of 10–45% in the case of powdery detergent compositions and in an amount of 20–50% in the case of liquid detergent compositions. When the detergent composition according to the present invention is a bleaching detergent or a detergent for automatic dish washers, these surfactants may be added usually in an amount of 1–10%, with 1–5% being preferred.

(2) Divalent metal ion scavengers

Examples of divalent metal ion scavengers include condensed phosphates such as tripolyphosphates, pyrrophosphates and orthophosphates; aluminosilicates such as zeolite; layered synthetic crystalline silicates; nitrilotriacetates, ethylenediaminetetraacetates, citrates, isocitrates and polyacetal carboxylates.

These divalent metal ion scavengers may be added in an amount of 0–50%, preferably 5–40%. It is more desired to use a phosphorus-free divalent metal ion scavenger.

(3) Alkali agents and inorganic salts

Examples of these include silicates, carbonates, sesquicarbonates, sulfates and alkanol amines.

They may be added in an amount of 0–80%, preferably 1–40%.

(4) Resoiling preventives

Exemplary resoiling preventives include polyethylene glycol, polyacrylates, polyacrylic acid copolymers, polyvinyl alcohol, polyvinyl pyrrolidone and carboxymethylcellulose. Some resoiling preventives also serve as divalent metal ion scavengers.

They may be added in an amount of 0–10%, preferably 1–5%.

(5) Enzymes

Examples of enzymes include cellulase, amylases other than liquefying alkaline α-amylase, lipase, hemicellulase, β-glycosidase, glucose oxidase, cholesterol oxidase and protease.

(6) Scavengers or reducing agents for available chlorine in tap water

Examples of scavengers for available chlorine include ammonium sulfate, urea, guanidine hydrochloride, guanidine carbonate, guanidine sulfamate, thiourea dioxide, monoethanolamine, diethanolamine, triethanolamine, amino acids typified by glycine and sodium glutamate, proteins such as bovine serum albumin and casein, protein hydrolysate, meat extract and fish meat extract.

Illustrative reducing agents include alkaline metal salts and alkaline earth metal salts such as thiosulfates, sulfites and dithionites. Rongalit C. Sulfites are particularly preferred, because they can stabilize enzymes in washing liquids.

(7) Bleaching agent

Illustrative bleaching agents includes percarbonates, perborates, sulfonated zinc phthalocyanates or sulfonated aluminum phthalocyanates and hydrogen peroxide. For a bleaching detergent, sodium percarbonate is particularly effective. These bleaching agents may be added in an amount of 1–95 wt. %, more preferably 5–95 wt. %, particularly 20–95 wt. %.

(8) Fluorescent dyes

Fluorescent dyes ordinarily employed in detergents.

(9) Solubilizing agents

For liquid detergents, solubilizing agents exemplified below can be employed:

Lower alcohols such as ethanol; lower alkylbenzene sulfonates such as benzene sulfonates and p-toluene sulfonates; and polyols such as propylene glycol.

(10) Other additives

Furthermore, each detergent composition according to the present invention can contain at need one or more of common detergent components such as conventionally-known perfumes, caking preventives, enzyme activators, antioxidants, antiseptics, colorants, blueing agents, bleaching activators, enzyme stabilizers and phase adjusters.

Each detergent composition according to the present invention can be produced in a manner known per se in the art by using the liquefying alkaline α-amylase and one or more of the above-described known detergent components in combination. The form of the detergent can be chosen depending on the application purpose. Exemplary forms include liquid, powder and granules. The detergent composition according to the present invention can be used as a laundry detergent, bleaching detergent, automatic dish-washing detergent, drainpipe cleaner, artificial teeth detergent or the like. It is suited especially for use as a laundry detergent, bleaching detergent or automatic dish-washing detergent.

EXAMPLES

The present invention will next be described in more detail by the following examples. It should however be borne in mind that this invention is by no means limited to or by the examples.

EXAMPLE 1

On a medium containing 1% of soluble starch (potato-derived), 1.0% of polypepton, 0.5% of yeast extract, 0.1% of $KH_2PO_4$, 0.25% of $Na_2HPO_4 \cdot 12H_2O$, 0.02% of $MgSO_4 \cdot 7H_2O$, 0.02% of $CaCl_2 \cdot 2H_2O$, 0.001% of $FeSO_4 \cdot 7H_2O$, 0.0001% of $MnCl_2 \cdot 4H_2O$ and 1.0% of $Na_2CO_3$, the strain Bacillus sp. KSM-AP1378, which is described in Example 1 of Japanese Patent Laid-Open No. 108482/1991, was cultured aerobically at 30° C. for 3 days under shaking. The cells were removed from the culture medium, whereby a supernatant was obtained. Ammonium sulfate was then added to the supernatant to give 20% saturation, followed by stirring at 5° C. for 2 hours to precipitate protein. The protein so precipitated was removed by centrifugation. Ammonium sulfate was further added to the resulting supernatant to give 40% saturation, followed by stirring at 5° C. for 12 hours to precipitate protein. The precipitate was collected by centrifugation and suspended in a 10 mM tris-hydrochloric acid buffer (pH 8), followed by dialysis against the buffer for 24 hours. The retentate was thereafter fractionated by gel filtration (TSK-G3000SW column) on a high-performance liquid chromatograph, whereby active fractions were collected and combined. The active fractions so combined were concentrated using an ultrafiltration membrane, followed by dialysis against a 10 mM tris-hydrochloric acid buffer (pH 8) overnight. As a result of sodium-dodecylsulfate (SDS) polyacrylamide gel electrophoresis (gel concentration: 7.5%), the purified enzyme was obtained at a single band. The yield of the active fractions was about 6.4%.

The enzymes so obtained had the enzymatic properties as described above.

EXAMPLE 2

A detergent containing the liquefying alkaline α-amylase according to the present invention and a detergent containing a conventional enzyme having α-amylase activity was compared in detergency. Incidentally, the preparation method of the DNS reagent, the measuring and calculation methods of enzymatic activity, the preparation method of soiled fabrics and the determination method of detergency, which will be referred to subsequently herein, will be described below.

[Preparation Method of the DNS Reagent]

In 200 ml of deionized water, 16 g of sodium hydroxide were dissolved. DNS (5 g) was gradually added to and dissolved in the resulting solution. After DNS had been dissolved completely, 300 g of sodium potassium tartrate were added. After they were dissolved completely, deionized water was added in a volume to give a total volume of 1,000 ml.

[Measuring method of degradation activity on soluble starch (determination of an amount of α-amylase to be added)]

(1) Substrate

A 0.5% aqueous solution of potato-derived soluble starch (product of Wako Pure Chemical Industries, Ltd.)

(2) Preparation of a substrate solution

In 100 ml of deionized water, 1.0 g of the potato-derived soluble starch (product of Wako Pure Chemical Industries, Ltd.) was dissolved.

(3) Enzyme assay

In a test tube, 0.5 ml of the substrate solution was charged, followed by the addition of 0.4 ml of a 50 mM phosphate buffer (pH 7.0) and 0.1 ml of a suitably-diluted enzyme solution. The reaction mixture was incubated at 40° C. for 30 minutes. After the completion of the reaction, 1 ml of the DNS reagent was added to the reaction mixture, followed by the development of a color in boiling water for exactly 5 minutes. Immediately after the color development, the reaction mixture was allowed to cool down in an ice-water bath and then added with 4 ml of deionized water. They were mixed thoroughly and the absorbance of the sample at 535 nm was measured promptly.

(4) Preparation of blank

In a test tube, 0.5 ml of the substrate solution was charged, followed by the addition of 0.4 ml of a 50 mM phosphate buffer (pH 7.0) and 1 ml of the DNS reagent. The resultant mixture was subjected to color development in boiling water for exactly 5 minutes. Immediately after the color development, the reaction mixture was allowed to cool down in an ice-water bath and then added with 4 ml of deionized water. They were mixed thoroughly and the absorbance of the blank at 535 nm was measured promptly.

(5) Preparation of a calibration curve

In a test tube, 0.5 ml of the substrate solution was charged, followed by the addition of 0.4 ml of 50 mM phosphate (pH 7.0). To the resulting solution, 0.1 ml of a glucose solution for a calibration curve was added to give a glucose concentration of 260–1500 µM. To the resulting solution, 1 ml of the DNS reagent was added, followed by the development of a color in boiling water for exactly 5 minutes. Immediately after the color development, the solution was allowed to cool down in an ice-water bath. The resulting solution, after cooling, was added with 4 mg of deionized water, followed by thorough mixing. The absorbance of the solution at 535 nm was then measured promptly. On a graph, the glucose concentration was plotted as abscissa and the absorbance as ordinate, whereby the slope of those linear plots was determined. A conversion factor (F) was calculated in accordance with the following formula:

$$F = [1/(slope)] \times [1/15] \times [1/6.1]$$

The degradation activity against amylose was calculated in accordance with the following formula:

| Activity (U/litter) = | δ absorbance × F × dilution rate |
|---|---|
| (δ absorbance = | the absorbance of sample − the absorbance of blank) |

[Preparation method of a fabric artificially soiled with curry]

A curry ("Bon Curry Gold, medium hot", trade name; product of OTSUKA SHOKUHIN CO., LTD) was chopped in a mixer. A cotton fabric was brought into contact with the chopped curry and then brushed to remove any extra curry. From the fabric, 10 cm×10 cm test pieces were cut out.

[Evaluation method of detergency]

The 460 nm reflectance of the cotton fabric before the soiling and those of the soiled piece before and after washing were measured by a self-registering colorimeter (manufactured by Shimadzu Corporation) and the detergency was evaluated from the detergency (%) calculated in accordance with the following formula:

$$\text{Detergency (\%)} = \frac{(\text{reflectance after washing} - \text{reflectance before washing})}{\text{reflectance of unsoiled cotton fabric} - \text{reflectance before washing})}$$

[Preparation of a liquid detergent]

A solution having a 5-fold concentration of the composition shown in Table 3 was prepared, followed by the pH adjustment to 7.0 with 1N hydrochloric acid. The pH-adjusted solution was diluted with deionized water to give the concentrations as shown in Table 3, whereby a liquid detergent having pH 7.0 was obtained.

TABLE 3

| Component | Amount added (wt. %) |
|---|---|
| Nonionic surfactant*[1] | 20 |
| Anionic surfactant*[2] | 20 |
| Citric acid | 5 |
| Monoethanolamine | 5 |
| Polyethylene glycol (average molecular weight = about 10,000) | 1 |
| Ethanol | 5.0 |
| Water | balance |
| Total | 100 |

*[1]Polyoxyethylene alkyl ether in which the average number of carbon atoms in the (linear) alkyl group was 12 and the number of moles of added ethylene oxide was 7.
*[2]Sodium polyoxyethylene alkylsulfate having linear $C_{12-14}$ alkyl groups and 2.5 moles on average of added ethylene oxide.

To each of 1 l portions of 4° DH water, 1.3 ml of the liquid detergent so obtained were added. Various α-amylases were added to the resulting solution at pH 7.0, respectively, to give an enzyme concentration of 150 U/l (note: the volume-up solution by the addition of each enzyme solution was ignored because the amount of the added enzyme solution was actually as little as 1 ml or less). Each fabric artificially soiled with the curry was dipped in 1 l of one of the detergent solutions which had been adjusted to 30° C. The detergent solution and the fabric dipped therein were left over for 30 minutes and were then transferred, as were, to a stainless steel beaker (1 l) for a Terg-O-Tometer. They were stirred at 20° C. and 100 rpm for 10 minutes on the Terg-0-Tometer. After the fabric was rinsed thoroughly with running water and then ironed, its reflectance was measured, thereby determining the percent detergency of the detergent. The results are shown in Table 4. As is apparent from Table 4, the detergent containing the liquefying alkaline α-amylase of the present invention had superior detergency to the detergents added with the conventional α-amylases, respectively, even if they had the same activity.

TABLE 4

| | α-amylase* | Optimum pH | Isoelectric point | Reaction Characteristics | Detergency (%) |
|---|---|---|---|---|---|
| Invention Product 1 | (1) | 8.5 | 9.2 | Liquefying | 80 |
| Comparative Product 1 | (2) | 6.1 | 5.4 | Liquefying | 60 |
| Comparative Product 2 | (3) | 10.0 | 4.9 | Saccharifying | 70 |
| Comparative Product 3 | (4) | 5.2 | 3.7 | Saccharifying | 55 |

TABLE 4-continued

|  | α-amylase* | Optimum pH | Isoelectric point | Reaction Characteristics | Detergency (%) |
|---|---|---|---|---|---|
| Comparative Product 4 | (5) | 7.0 | 6.5 | Saccharifying | 55 |
| Comparative Product 5 | (6) | 5.6 | 7.2 | Liquefying | 55 |
| Comparative Product 6 | Not added | — | — | — | 50 |

*(1) Derived from Bacillus sp. KSM-AP1378 and having a molecular weight of about 50,000 (the amylase according to the present invention).
(2) Derived from *Bacillus subtilis* (product of Wako Pure Chemical Industries, Ltd.).
(3) Derived from Bacillus sp. KSM-AP1378 and having a molecular weight of about 200,000 (the enzyme disclosed in Japanese Patent Laid-Open No. 108482/1991 and having both pullulanase activity and α-amylase activity).
(4) Derived from *Aspergillus oryzae* (product of Sigma Chemical Co., Ltd.)
(5) Derived from porcine pancreas (product of Sigma Chemical Co., Ltd.)
(6) Derived from *Bacillus licheniformis* ("Termamyl", product of Novo Industry A/S)

EXAMPLE 3

Detergent particles which were prepared in the manner described below and a granulated product of alkaline α-amylase were dry-blended, whereby granular detergents having compositions shown in Table 5 were prepared, respectively. Their detergency was evaluated.

[Production method of the detergents]

(1) A slurry mixture having a water content of 50% and formed of the components (other than α-amylase) shown in Table 5 except 10% of zeolite 4A, the fluorescent brightener and the perfume was prepared and spray-dried, whereby preformed detergent particles were obtained. Those particles were placed in a high-speed mixer and then granulated, followed by the addition of the remaining components, whereby a granular detergent was obtained (other than Invention Products 3 and 6).

(2) A slurry mixture having a water content of 50% and formed of the components (other than α-amylase) of Invention Product 3 shown in Table 5 except 10% of zeolite 4A, the oil-absorbing carrier, the fluorescent brightener and the perfume was prepared and spray-dried, whereby preformed detergent particles were obtained. Those particles were placed in a high-speed mixer and then granulated, followed by the addition of the remaining components, whereby a granular detergent was obtained (Invention Product 3).

(3) While stirring in a Redige mixer the components (other than α-amylase) of Invention Product 6 shown in Table 5 except the nonionic surfactant, 10% of zeolite 4A, the fluorescent brightener and the perfume, the nonionic surfactant was gradually added. After the addition, the remaining components were added, whereby a granular detergent was obtained (Invention Product 6).

(4) The liquefying alkaline α-amylase which had been obtained in Example 1 was granulated with sodium sulfate and a small quantity of polyethylene glycol. Granules so obtained were dry-blended with the granular detergents obtained in the above (1)–(3), respectively, whereby granular detergents having the compositions shown in Table 5 were obtained.

Incidentally, the average particle size and bulk density of each of the granular detergents so obtained are indicated below.

Invention Products 2, 4, 5, 7-9, Comparative Products 7-9:

Average particle size: 400–500 μm,

Bulk density: 750–780 g/cm$^3$

Invention Product 3:

Average particle size: 400 μm,

Bulk density: 770 g/cm$^3$

Invention Product 6:

Average particle size: 450 μm,

Bulk density: 800 g/cm$^3$

[Evaluation method]

To 4° DH water, each granular detergent so obtained was added, whereby a 0.833% aqueous detergent solution was prepared. A fabric which had been soiled artificially with curry as in Example 2 was dipped in 1 l of the detergent solution controlled at 30° C. The detergent solution with the fabric dipped therein was left over and then transferred, as were, to a stainless steel beaker (1 l) for a Terg-o-Tometer. They were stirred at 20° C. and 100 rpm for 10 minutes on the Terg-o-Tometer. The fabric was rinsed thoroughly with running water and then ironed. In a similar manner to Example 2, the reflectance of the fabric was measured, thereby determining the percent detergency of the detergent. The results are shown in Table 5.

TABLE 5

| Composition (wt. %) | Invention Product | | | | | | | | Comparative Product | | |
|---|---|---|---|---|---|---|---|---|---|---|---|
|  | 2 | 3 | 4 | 5 | 6 | 7 | 8 | 9 | 7 | 8 | 9 |
| Alkaline α-amylase*$^1$ | 2 | 2 | 5 | 6 | 6 | 2 | 5 | 6 | 0 | 0 | 0 |
| Beef tallow soap*$^2$ | 0 | 0 | 0 | 0 | 1.5 | 0.5 | 0 | 0 | 0.5 | 0 | 0 |
| Sodium carbonate | 12 | 12 | 12 | 12 | 12 | 12 | 12 | 12 | 12 | 12 | 12 |
| Potassium carbonate | 0 | 5 | 0 | 0 | 0 | 0 | 0 | 3 | 0 | 0 | 0 |
| JIS No. 2 sodium silicate | 10 | 10 | 10 | 10 | 0 | 10 | 10 | 10 | 0 | 0 | 0 |
| Zeolite 4A*$^3$ | 30 | 20 | 30 | 30 | 30 | 20 | 20 | 20 | 30 | 30 | 30 |

TABLE 5-continued

| Composition (wt. %) | Invention Product | | | | | | | | Comparative Product | | |
|---|---|---|---|---|---|---|---|---|---|---|---|
| | 2 | 3 | 4 | 5 | 6 | 7 | 8 | 9 | 7 | 8 | 9 |
| Nonionic surfactant*[4] | 0 | 10 | 0 | 0 | 20 | 3 | 3 | 3 | 0 | 0 | 0 |
| Anionic surfactant a*[5] | 20 | 10 | 18 | 18 | 0 | 20 | 20 | 20 | 20 | 20 | 20 |
| Anionic surfactant b*[6] | 20 | 10 | 20 | 20 | 0 | 10 | 10 | 10 | 20 | 20 | 20 |
| Polyethylene glycol*[7] | 1 | 1 | 1 | 1 | 1 | 1 | 1 | 1 | 1 | 1 | 1 |
| Sodium polyacrylate*[8] | 2 | 2 | 2 | 2 | 2 | 2 | 2 | 2 | 2 | 2 | 2 |
| Oil-absorbing carrier*[9] | 0 | 5 | 0 | 0 | 10 | 0 | 0 | 0 | 0 | 0 | 0 |
| Fluorescent brightener*[10] | 0.3 | 0.3 | 0.3 | 0.3 | 0.3 | 0.3 | 0.3 | 0.3 | 0.3 | 0.3 | 0.3 |
| Perfume | 0.2 | 0.2 | 0.2 | 0.2 | 0.2 | 0.2 | 0.2 | 0.2 | 0.2 | 0.2 | 0.2 |
| Sodium sulfate | | | | Balance | | | | | | Balance | |
| Total | 100 | 100 | 100 | 100 | 100 | 100 | 100 | 100 | 100 | 100 | 100 |
| Detergency (%) | 74 | 72 | 77 | 81 | 82 | 75 | 80 | 81 | 60 | 61 | 61 |

*[1]Derived from Bacillus sp. KSM-AP1378 and having a molecular weight of about 50,000 (liquefying alkaline α-amylase) and a specific activity of 3,000 U/g.
*[2]Having 12–14 carbon atoms and has a neutralization rate of 100%.
*[3]Having an average particle size of 0.9 μm.
*[4]Polyoxyethylene alkyl ether (average moles of added EO = 8, carbon atoms of the alkyl group = 12)
*[5]Sodium linear alkylbenzene sulfonate (carbon atoms of the alkyl group = 12–16)
*[6]Sodium alkylsulfate (carbon atoms of the alkyl group = 12–14)
*[7]Having an average molecular weight of about 8,000. The amount added does not include that in the α-amylase particles.
*[8]Having an average molecular weight of about 13,000.
*[9]"Tokuseal NR" (trade name, product of Tokuyama Soda Co., Ltd.)
*[10]"Chinopearl CBS" [trade name, product of CIBA-GEIGY (Japan), Ltd.]

EXAMPLE 4

Liquid detergents having the compositions shown in Table 6 were prepared, respectively. In a similar manner to Example 2, a washing test was conducted to determine the percent detergency of each of the detergents. The results are shown in Table 6.

TABLE 6

| Composition (wt. %) | Invention product | | | Comparative product | |
|---|---|---|---|---|---|
| | 10 | 11 | 12 | 10 | 11 |
| Alkaline α-amylase*[1] | 2 | 5 | 5 | 0 | 0 |
| Citric acid | 2 | 2 | 2 | 2 | 2 |
| Nonionic surfactant*[2] | 20 | 15 | 20 | 20 | 15 |
| Anionic surfactant a*[3] | 20 | 10 | 15 | 20 | 20 |
| Polyethylene glycol*[4] | 1 | 1 | 1 | 1 | 1 |
| Monoethanolamine | 3 | 3 | 3 | 3 | 3 |
| Fluorescent brightener*[5] | 0.1 | 0.1 | 0.1 | 0.1 | 0.1 |
| Ethanol | 5 | 5 | 5 | 5 | 5 |
| Water | | Balance | | | Balance |
| Total | 100 | 100 | 100 | 100 | 100 |
| Detergency (%) | 70 | 68 | 71 | 50 | 52 |

*[1]Derived from Bacillus sp. KSM-AP1378 and having a molecular weight of about 50,000 (liquefying alkaline α-amylase) and a specific activity of 3,000 U/g.
*[2]Polyoxyethylene alkyl ether (average moles of added EO = 7, carbon atoms of the alkyl group = 12–14)
*[3]Sodium polyoxyethylene alkylsulfate (average moles of added EO = 2.5, carbon atoms of the alkyl group = 12–14)
*[4]Having an average molecular weight of about 8,000.
*[5]"Chinopearl CBS" [trade name, product of CIBA-GEIGY (Japan), Ltd.]

EXAMPLE 5

Among the components shown in Table 7, the 40% aqueous solution of sodium polyacrylate, and the sodium linear alkylbenzene sulfonate or the nonionic surfactant were added while stirring and mixing the sodium percarbonate and the soda ash (dense ash). To the resulting mixture, the granulate of the liquefying alkaline α-amylase, which had been obtained in Example 3, was added and stirred until the resulting solution became uniform in toto, whereby a bleaching detergent shown in Table 7 was obtained.

The percent detergency of the bleaching detergent was determined under the conditions as in Example 3 except that a 0.05% aqueous solution was prepared and stirring was conducted at 40° C. for 30 minutes. The results are also shown in Table 7.

TABLE 7

| | | | | (wt. %) |
|---|---|---|---|---|
| | Invention product | | | Comparative product |
| | 13 | 14 | 15 | 12 |
| Sodium percarbonate*[1] | 80.0 | 80.0 | 80.0 | 80.0 |
| Sodium carbonate (dense ash) | 16.5 | 16.0 | 16.5 | 17.0 |
| Anionic surfactant*[2] | 2.0 | 2.0 | — | 2.0 |
| Nonionic surfactant*[3] | — | — | 2.0 | — |
| Sodium polyacrylate*[4] | 1.0 | 1.0 | 1.0 | 1.0 |
| Amylase (granulate) | 0.5 | 1.0 | 0.5 | 0 |
| Detergency (%) | 55 | 58 | 54 | 48 |

*[1]Particle size: 500–700 μm
*[2]Sodium linear alkylbenzene sulfonate (having 12–14 carbon atoms)
*[3]Polyoxyethylene alkyl ether (carbon atoms of the alkyl group = 12–14, average mole of added EO = 12)
*[4]Average molecular weight of about: 8,000.

EXAMPLE 6

In a similar manner to Example 5, automatic dishwashing detergents having the compositions shown in Table 8 were prepared, respectively.

TABLE 8

| | Invention product (wt. %) | | | |
|---|---|---|---|---|
| | 16 | 17 | 18 | 19 |
| "Pullulonic L-61"*[1] | 4 | — | 4 | 4 |
| "Softanol EP-7085"*[2] | — | 4 | — | — |
| Trisodium citrate | 30 | 30 | — | — |
| EDTA | — | — | 30 | — |
| Sodium tripolyphosphate | — | — | — | 30 |
| Sodium percarbonate | 20 | 20 | 20 | 20 |
| Sodium carbonate | 20 | 20 | 20 | 20 |
| No. 1 sodium silicate | 10 | 10 | 10 | 10 |
| Sodium polyacrylate*[3] | 4 | 4 | 4 | 4 |
| Sodium sulfate | Balance | | | |
| Amylase (granulate) | 3 | 3 | 3 | 3 |

*[1]Polyoxyethylene-polyoxypropylene copolymer (Average molecular weight: 2,000, product of Asahi Denka Kogyo K.K.)
*[2]7 moles ethylene oxide/8.5 moles propylene oxide adduct of $C_{12-14}$ sec-alcohol (product of Nippon Shokubai Co., Ltd.)
*[3]Having an average molecular weight of about 8,000.

The detergency of each automatic dish-washing detergents so obtained was evaluated under the conditions described below. As a result, it was found that each of the detergents exhibited excellent dish-washing effects, thereby showing superiority to detergents free of the amylase.

[Preparation of soiled dishes] Newly boiled sticky rice was allowed to stand at room temperature for 30 minutes and then, 3 g of the rice were spread under pressure on a porcelain dish having a diameter of 25 cm. The dish was air-dried at room temperature for 24 hours. Six dishes were prepared in this way for the test described below.

[Evaluation method of the detergency against boiled rice soil]

The wash liquor remaining after the washing and containing rice was subjected to the iodo-starch reaction, whereby the detergency was macroscopically determined.

[Testing method of detergency]

Washing conditions:

The washer employed: Full automatic dish washer "NP-720" (trade name, manufactured by Matsushita Electric Industries Co., Ltd.) of the type that an aqueous detergent solution is sprayed from rotary nozzles to wash dishes and the like placed on an upper surface defined by its spray flow lines.

Washing temperature: gradually raised from 5° C. to 55° C.

Water used: water having a hardness of 3.5° DH.

Concentration of the detergent: 0.2 wt. %.

Washing time: 20 minutes washing, followed by 20 minutes rinsing.

Amount of water circulated upon washing: 2.5 l.

The liquefying alkaline α-amylase according to the present invention has liquefying activity which permits high-random degradation of substrates, such as starches and starchy polysaccharides, than the conventional alkaline α-amylases. It has an optimum pH on the alkaline side (8.0–10.0) and moreover, is extremely stable in a still wider pH range. Its optimum temperature is 45° C–55° C. so that it retains excellent thermal stability up to 50° C. Furthermore, its activity is hardly inhibited by other detergent components such as a surfactant. The conventionally-known alkaline α-amylases have an isoelectric point of about 3.0–8.0, while the liquefying alkaline α-amylase according to the present invention has an exceptionally high isoelectric point exceeding 8.5 (8.7–9.7, specifically around 9.2). Making use of such characteristics of this enzyme, it can readily be obtained in a purified form by gel isoelectric focusing electrophoresis, density gradient isoelectric point, ion exchange chromatography or the like. It has therefore an extremely great industrial significance.

Detergent compositions containing the liquefying alkaline α-amylase of the present invention have excellent detergency especially against the soil of smeared food.

The superior detergency of the liquefying alkaline α-amylase according to the present invention to the conventional amylases is considered to be attributable to the influence of the high isoelectric point in addition to the characteristic of the liquefying type, that is, high-random degradation. Described specifically, fibers are generally electrified negative in water. When a wash liquor has a high pH, an enzyme is also electrified negative provided that the enzyme has a low isoelectric point. As a consequence, the fibers and the enzyme become repulsive each other. The liquefying alkaline α-amylase according to the present invention, however, has a high isoelectric point so that it is not electrified negative in the wash liquor. Repulsion between the enzyme against the soil on the surface of the fiber is hence reduced, thereby probably contributing to improved detergency.

We claim:

1. A liquefying alkaline α-amylase having the following enzymatic properties:
   1) action:
      hydrolyzes 1,4-α-glucosidic linkages in starches, amylose, amylopectin and partial degradation products thereof and from amylose, forms glucose (G1), maltose (G2), maltotriose (G3), maltotetraose (G4), maltopentaose (G5) and maltohexaose (G6), but does not act on pullulan;
   2) isoelectric point:
      has an isoelectric point of about 9.2 when measured by isoelectric focusing electrophoresis.

2. A liquefying alkaline α-amylase according to claim 1, which has an optimum pH for activity from 8.0 to 10.0.

3. A liquefying alkaline α-amylase according to claim 1, which is substantially free from activity inhibition by surfactants selected from the group consisting of sodium linear alkylbenzene sulfonates, sodium alkylsulfate esters, sodium polyoxyethylene alkylsulfate esters, sodium alkylsulfonates, soaps, and polyoxyethylene alkyl ethers.

4. A liquefying alkaline α-amylase according to claim 1, which has a sequence of Asn-Gly-Thr-Met-Met-Gln-Tyr-Phe-Glu-Trp in its N-terminal amino acid region.

5. A liquefying alkaline α-amylase having the following enzymatic properties:
   1) action:
      hydrolyzes 1,4-α-glucosidic linkages in starches, amylose, amylopectin and partial degradation products thereof and from amylose, forms glucose (G1), maltose (G2), maltotriose (G3), maltotetraose (G4), maltopentaose (G5) and maltohexaose (G6), but does not act on pullulan;
   2) isoelectric point:
      has an isoelectric point of about 9.2 when measured by isoelectric focusing electrophoresis;
   3) acting pH:
      acts in a pH range of from 5.0 to 11.0;
   4) pH stability:
      stable in a pH range of from 6.5 to 10.0;
   5) acting temperature range:
      acts in a temperature range of from 20° C. to 80° C.;

6) thermal stability:

stable at temperatures of 50° C. or lower when treated for 30 minutes in a glycine-salt-sodium hydroxide buffer having a of pH 8.5;

7) molecular weight:

has a molecular weight of 50,000±5,000 as measured by sodium dodecyl sulfate polyacrylamide gel electrophoresis;

8) effect of surfactants:

substantially free from activity inhibition by surfactants selected from the group consisting of sodium linear alkylbenzene sulfonates, sodium alkylsulfate esters, sodium polyoxyethylene alkylsulfate esters, sodium alkylsulfonates, soaps, and polyoxyethylene alkyl ethers.

6. A liquefying alkaline α-amylase according to claim 5, which and has an optimum pH for activity between 8.0 to 9.0.

7. A liquefying alkaline α-amylase according to claim 5, which has an optimum acting temperature range from 45° C. to 55° C.

8. A liquefying alkaline α-amylase according to claim 5, which has a sequence of Asn-Gly-Thr-Met-Met-Gln-Tyr-Phe-Glu-Trp in its N-terminal amino acid region.

9. A process for the preparation of a liquefying alkaline α-amylase, comprising the steps of:

(a) culturing a liquefying-alkaline-α-amylase-producing bacterium belonging to the genus Bacillus; and (b) isolating the liquefying alkaline α-amylase from the resulting culture;

wherein said liquefying alkaline α-amylase has the following enzymatic properties:

1) action:

hydrolyzes 1,4-α-glucosidic linkages in starches, amylose, amylopectin and partial degradation products thereof and from amylose, forms glucose (G1), maltose (G2), maltotriose (G3), maltotetraose (G4), maltopentaose (G5) and maltohexaose (G6), but does not act on pullulan;

2) isoelectric point:

has an isoelectric point of about 9.2 when measured by isoelectric focusing electrophoresis.

10. A process according to claim 9, wherein said liquefying-alkaline-α-amylase-producing bacterium is *Bacillus sp.* KSM-AP1378 (FERM BP-3048).

11. A detergent composition, comprising:

(a) a surfactant selected from the group consisting of anionic surfactants, nonionic surfactants, and mixtures thereof; and (b) a liquefying alkaline α-amylase having the following enzymatic properties:

1) action:

hydrolyzes 1,4-α-glucosidic linkages in starches, amylose, amylopectin and partial degradation products thereof and from amylose, forms glucose (G1), maltose (G2), maltotriose (G3), maltotetraose (G4), maltopentaose (G5) and maltohexaose (G6), but does not act on pullulan;

2) isoelectric point:

has an isoelectric point of about 9.2 when measured by isoelectric focusing electrophoresis.

12. A detergent composition according to claim 11, wherein said liquefying alkaline α-amylase has an optimum pH of from 8.0 to 10.0.

13. A detergent composition according to claim 11, wherein said liquefying alkaline α-amylase is substantially free from activity inhibition by surfactants selected from the group consisting of sodium linear alkylbenzene sulfonates, sodium alkylsulfate esters, sodium polyoxyethylene alkylsulfate esters, sodium alkylsulfonates, soaps, and polyoxyethylene alkyl ethers.

14. A detergent composition according to claim 11, which has a sequence of Asn-Gly-Thr-Met-Met-Gln-Tyr-Phe-Glu-Trp in its N-terminal amino acid region.

15. A detergent composition according to claim 11, wherein said liquefying alkaline α-amylase has been produced by *Bacillus sp.* KSM-AP1378 (FERM BP-3048).

16. A detergent composition according to claim 11, wherein said surfactant comprises 0.5 to 60 wt % of said composition.

17. A detergent composition according to claim 11, wherein said composition contains 1 to 10,000 U/g of said liquefying alkaline α-amylase.

18. A detergent composition according to claim 11, wherein said liquefying alkaline α-amylase has the following additional enzymatic properties:

3) acting pH:

acts in a pH range of from 5.0 to 11.0;

4) pH stability:

stable in a pH range of from 6.5 to 10.0;

5) acting temperature range:

acts in a temperature range of from 20° C. to 80° C.;

6) thermal stability:

stable at temperatures of 50° C. or lower when treated for 30 minutes in a glycine-salt-sodium hydroxide buffer having a of pH 8.5;

7) molecular weight:

has a molecular weight of 50,000±5,000 as measured by sodium dodecyl sulfate polyacrylamide gel electrophoresis;

8) effect of surfactants:

substantially free from activity inhibition by surfactants selected from the group consisting of sodium linear alkylbenzene sulfonates, sodium alkylsulfate esters, sodium polyoxyethylene alkylsulfate esters, sodium alkylsulfonates, soaps, and polyoxyethylene alkyl ethers.

19. A detergent composition according to claim 18, wherein said liquefying alkaline α-amylase has an optimum pH between 8.0 to 9.0.

20. A detergent composition according to claim 18, wherein said liquefying alkaline α-amylase has an optimum acting temperature range from 45° C. to 55° C.

21. A detergent composition according to claim 18, which has a sequence of Asn-Gly-Thr-Met-Met-Gln-Tyr-Phe-Glu-Trp in its N-terminal amino acid region.

22. A detergent composition according to claim 18, wherein said composition contains 1 to 10,000 U/g of said liquefying alkaline α-amylase.

23. A detergent composition according to claim 18, wherein said surfactant comprises 0.5 to 60 wt % of said composition.

* * * * *